United States Patent
Coe (10) Patent No.: US 12,403,124 B2
(45) Date of Patent: Sep. 2, 2025

(54) CENTRAL NERVOUS SYSTEM HEALTH SUPPLEMENT

(71) Applicant: William B. Coe, Wrightwood, CA (US)

(72) Inventor: William B. Coe, Wrightwood, CA (US)

(*) Notice: Subject to any disclaimer, the term of this patent is extended or adjusted under 35 U.S.C. 154(b) by 933 days.

(21) Appl. No.: 17/644,069

(22) Filed: Dec. 13, 2021

(65) Prior Publication Data
US 2022/0202766 A1 Jun. 30, 2022

Related U.S. Application Data

(60) Provisional application No. 63/211,420, filed on Jun. 16, 2021, provisional application No. 63/131,591, filed on Dec. 29, 2020.

(51) Int. Cl.

| | | |
|---|---|---|
| A61K 31/352 | (2006.01) | |
| A61K 9/00 | (2006.01) | |
| A61K 9/20 | (2006.01) | |
| A61K 31/197 | (2006.01) | |
| A61K 31/202 | (2006.01) | |
| A61K 31/405 | (2006.01) | |
| A61K 31/575 | (2006.01) | |
| A61K 31/685 | (2006.01) | |
| A61K 31/706 | (2006.01) | |
| A61K 36/42 | (2006.01) | |
| A61K 36/79 | (2006.01) | |
| A61K 38/06 | (2006.01) | |
| A61K 47/10 | (2017.01) | |
| A61K 47/12 | (2006.01) | |
| A61P 25/16 | (2006.01) | |
| A61P 25/28 | (2006.01) | |

(52) U.S. Cl.
CPC ............ *A61K 31/352* (2013.01); *A61K 9/006* (2013.01); *A61K 9/205* (2013.01); *A61K 9/2068* (2013.01); *A61K 31/197* (2013.01); *A61K 31/202* (2013.01); *A61K 31/405* (2013.01); *A61K 31/575* (2013.01); *A61K 31/685* (2013.01); *A61K 31/706* (2013.01); *A61K 36/42* (2013.01); *A61K 36/79* (2013.01); *A61K 38/063* (2013.01); *A61K 47/10* (2013.01); *A61K 47/12* (2013.01); *A61P 25/16* (2018.01); *A61P 25/28* (2018.01)

(58) Field of Classification Search
CPC ...... A61K 31/352; A61K 9/006; A61K 9/205; A61K 9/2068; A61K 31/197; A61K 31/202; A61K 31/405; A61K 31/575; A61K 31/685; A61K 31/706; A61K 36/42; A61K 36/79; A61K 38/063; A61K 47/10; A61K 47/12; A61K 9/0056; A61K 9/2018; A61P 25/16; A61P 25/28
See application file for complete search history.

(56) References Cited

U.S. PATENT DOCUMENTS

2010/0151055 A1* 6/2010 Riess ................. A23L 27/86
426/271

OTHER PUBLICATIONS

Vang, S.; Burns, K.; Steer, C.; Low, W. The Unexpected Uses of Urso- and Tauroursodeoxycholic Acid in the Treatment of Non-liver Diseases. Global Advances in Health and Medicine, 3 (3), pp. 58-69. (Year: 2014).*
Azevedo et al., 2009, Equal numbers of neuronal and nonneuronal cells make the human brain an isometrically scaled-up primate brain. J. Comp. Neurol. 513:532-541.
Bessis et al., 2007, Microglial control of neuronal death and synaptic properties. Glia 55:233-238.
Bruttger et al., Jul. 21, 2015, Genetic cell ablation reveals clusters of local self-renewing microglia in the mammalian central nervous system. Immunity 43:92-106.
Chari et al., 2002, Efficient recolonisation of progenitor-depleted areas of the CNS by adult oligodendrocyte progenitor cells. Glia 37:307-313.
Cronk et al., 2013, Microglia—the brain's busy bees. F1000Prime Rep. 5:53.
Doetsch et al., Sep. 1999, Regeneration of a germinal layer in the adult mammalian brain. Proc. Natl. Acad. Sci. U.S.A. 96:11619-11624.
Elmore et al., Apr. 16, 2014, Colony-stimulating factor 1 receptor signaling is necessary for microglia viability, unmasking a microglia progenitor cell in the adult brain. Neuron 82:380-397.
Elmore et al., Apr. 7, 2015, Characterizing newly repopulated microglia in the adult mouse: impacts on animal behavior, cell morphology, and neuroinflammation. PLoS ONE 10:e0122912.
Fischer et al., Feb. 2019, Old age-associated phenotypic screening for Alzheimer's disease drug candidates identifies sterubin as a potent neuroprotective compound from Yerba Santa. Redox Biol. 21:101089.
Herculano-Houzel, 2014, The glia/neuron ratio: how it varies uniformly across brain structures and species and what that means for brain physiology and evolution. Glia 62(9):1377-1391.
Hong et al., May 6, 2016, Complement and microglia mediate early synapse loss in Alzheimer mouse models. Science 352(6286):712-716.
Hong et al., Feb. 2016, New insights on the role of microglia in synaptic pruning in health and disease. Curr. Opin. Neurobiol. 36:128-134.
Honjo et al., Jun. 25, 1968, Diphtheria toxin-dependent adenosine diphosphate ribosylation of aminoacyl transferase II and inhibition of protein synthesis. J. Biol. Chem. 243(12):3553-3555.

(Continued)

*Primary Examiner* — Jessica Worsham
(74) *Attorney, Agent, or Firm* — Knobbe, Martens, Olson & Bear, LLP (57) ABSTRACT

An orally administered composition positively mitigates the progression of central nervous system diseases such as Alzheimer's, Parkinson's and Multiple Sclerosis. The composition consists of a lipid based blood brain barrier transport medium (Base Transport Sub-Formula) to which other elements (Functional Targeting Compound) may be integrated to mediate specific chemo-neurological dysfunction. It may be administered through the mouth as droplets a spray medium or a chewable tablet.

15 Claims, 1 Drawing Sheet

(56) References Cited

OTHER PUBLICATIONS

Johnson et al., 2003, De-intercalation of ethidium bromide and acridine orange by xanthine derivatives and their modulatory effect on anticancer agents: a study of DNA-directed toxicity enlightened by time correlated single photon counting. J. Biomol. Struct. Dyn. 20(5):677-686.

Kalderon et al., Oct. 1996, Severed corticospinal axons recover electrophysiologic control of muscle activity after x-ray therapy in lesioned adult spinal cord. Proc. Natl. Acad. Sci. U.S.A. 93:11185-11190.

Kettenmann et al., 2011, Physiology of microglia. Physiol. Rev. 91:461-553.

Kim et al., 2005, Microglia in health and disease. J. Neurosci. Res. 81:302-313.

Nimmerjahn et al., May 27, 2005, Resting microglial cells are highly dynamic surveillants of brain parenchyma in vivo. Science 308:1314-1318.

Parkhurst et al., Dec. 19, 2013, Microglia promote learning-dependent synapse formation through brain-derived neurotrophic factor. Cell 155:1596-1609.

Pineau et al., 2010, Astrocytes initiate inflammation in the injured mouse spinal cord by promoting the entry of neutrophils and inflammatory monocytes in an IL-1 receptor/MyD88-dependent fashion. Brain Behav. Immun. 24:540-553.

Silver et al., 2015, Central nervous system regenerative failure: role of oligodendrocytes, astrocytes, and microglia. Cold Spring Harb. Perspect. Biol. 2015;7:a020602.

Torres et al., Jul. 2016, Dynamic microglial modulation of spatial learning and social behavior. Brain Behav. Immun. 55:6-16.

Van Rooijen et al., 1990, Depletion and repopulation of macrophages in spleen and liver of rat after intravenous treatment with liposome-encapsulated dichloromethylene diphosphonate. Cell Tissue Res. 260:215-222.

Vasek et al., Jun. 23, 2016, A complement-microglial axis drives synapse loss during virus-induced memory impairment. Nature 534(7608):538-543.

Waisman et al., Oct. 2015, Homeostasis of microglia in the adult brain: review of novel microglia depletion systems. Trends Immunol. 36(10):625-636.

Wu et al., Oct. 2015, Microglia: dynamic mediators of synapse development and plasticity. Trends Immunol. 36(10):605-613.

Yajima et al., 1979, Demyelination and remyelination in the rat central nervous system following ethidium bromide injection. Lab. Invest. 41(5):385-392.

\* cited by examiner

CENTRAL NERVOUS SYSTEM HEALTH SUPPLEMENT

CROSS-REFERENCE TO RELATED APPLICATIONS

This application claims the benefit of U.S. Provisional Application Ser. No. 63/131,591, filed Dec. 29, 2020, titled CENTRAL NERVOUS SYSTEM HEALTH SUPPLEMENT and U.S. Provisional Application Ser. No. 63/211,420, filed Jun. 16, 2021, titled CENTRAL NERVOUS SYSTEM HEALTH SUPPLEMENT, both of which are hereby incorporated by reference herein in their entirety and for all purposes.

FIELD

An orally administered composition positively mitigates the progression of central nervous system diseases such as Alzheimer's, Parkinson's and Multiple Sclerosis. The composition consists of a lipid based blood brain barrier transport medium (Base Transport Sub-Formula) to which other elements (Functional Targeting Compound) may be integrated to mediate specific chemo-neurological dysfunction. It may be administered through the mouth as droplets a spray medium or a chewable tablet.

BACKGROUND

Central nervous system diseases include Parkinson's, Multiple Sclerosis and Dementia. Dementia has several categories including Alzheimer's and Lewy Body Dementia. Alzheimer's Dementia (AD) is the number six (#6) killer in the United States. Current U.S. health costs associated with this disease exceeds $300 billion. Estimates are that this cost will rise to $1.1 trillion by 2050. Every 65 seconds AD claims a new host in America. Of the top ten killers in the U.S. AD is the only one that has no therapeutic whatsoever.

AD is characterized by amyloid plaque and tau plaque. These plaques are characterized as toxic proteins coating the brain cell neurons and dendrites respectively. These plaques begin as participatory proteins generated within the brain as neuronal cells are birthed and grow; but the progression to becoming a toxic plaque which essentially strangles the brain cell from receiving and processing nutrition is not understood.

AD disease progression eventually leads to brain shrinkage, loss of the brain's modulating effect on the major organs of the body and death. AD progression is slow, spanning the years from early onset of symptoms which can be as young as age 30 to age 85, leaving the patient with an ever-growing loss of memory and physical vitality.

In vitro and in vivo studies of various chemical compounds aimed at dissolving the toxic plaques and/or slowing the progression of such plaque development have shown promise. However, the BBB has proven a formidable guardian to moving these early stage chemical compounds into the brain via the micro environment of the body's blood stream, i.e. the BBB three principal mechanisms filter and chemically modify these interventions such that they can no longer effectuate the in vitro/in vivo environment.

SUMMARY

Treatments that are effective against Parkinson's, Multiple Sclerosis and Dementia, e.g., Alzheimer's Dementia or Lewy Body Dementia, or other conditions impacted by amyloid plaque and/or tau plaque, are desirable. Accordingly, certain compositions that support health are provided, as are methods for administering the compositions.

Supporting brain health, mood, and energy are also desirable. Accordingly, certain compositions that support health are provided, as are methods for administering the compositions.

Accordingly, in a generally applicable first aspect (i.e., independently combinable with any of the aspects or embodiments identified herein), a pharmaceutical composition or dietary supplement or health supplement or other physiologically-acceptable formulation is provided comprising: sterubin; and a pharmaceutically or physiologically-acceptable carrier.

In an embodiment of the first aspect (i.e., independently combinable with any of the aspects or embodiments identified herein), the pharmaceutical composition or dietary supplement or health supplement or other physiologically-compatible formulation comprises 0.001%-20% by weight of sterubin.

In an embodiment of the first aspect (i.e., independently combinable with any of the aspects or embodiments identified herein), the pharmaceutical composition or dietary supplement or health supplement or other physiologically-compatible formulation is in a form of a chewable tablet.

In an embodiment of the first aspect (i.e., independently combinable with any of the aspects or embodiments identified herein), the pharmaceutical composition or dietary supplement or health supplement or other physiologically-compatible formulation is in a form of a spray for oral administration.

In an embodiment of the first aspect (i.e., independently combinable with any of the aspects or embodiments identified herein), the pharmaceutical composition or dietary supplement or health supplement or other physiologically-compatible formulation is in a form adapted to be delivered to the patient by inhalation in a form of a vapor, a mist, or an aerosol.

In an embodiment of the first aspect (i.e., independently combinable with any of the aspects or embodiments identified herein), the pharmaceutical composition or dietary supplement or health supplement or other physiologically-compatible formulation is in a form for administration at a dosage of 300 mg, in sublingual form for absorption under the tongue, wherein the form contains: 1) Sterubin-bio-concentrated, Yerba Santa (11.2 wt. %); 2) Gamma aminobutyric acid (10.7 wt. %); 3) tauroursodeoxycholic acid (10.7 wt. %); 4) Glutathione (9.7 wt. %); 5) Nicotinamide mononucleotide (9.5 wt. %); 6) Alpha-glyceryl phosphorylcholine (8.5 wt. %); 7) 5-hydroxytryptophan (5.5 wt. %); 8) Phosphatidylserine (4.8 wt. %); 9) Star Anis (2.5 wt. %); 10) Omega oil (11.5 wt. %); 11) Glycerin (11.4 wt. %); 12) Monk Fruit (2.8 wt. %); and 13) Magnesium Stearate (1.2 wt. %).

In a generally applicable second aspect (i.e., independently combinable with any of the aspects or embodiments identified herein), a method is provided of treatment of a central nervous system disease selected from the group consisting of Parkinson's Disease, Multiple Sclerosis, and Dementia, comprising: administering, to a patient in need thereof, an effective amount of sterubin.

In an embodiment of the second aspect (i.e., independently combinable with any of the aspects or embodiments identified herein), the Dementia is selected from the group consisting of Alzheimer's Disease and Lewy Body Dementia.

In a generally applicable third aspect (i.e., independently combinable with any of the aspects or embodiments identified herein), a method is provided of ameliorating, slowing onset, or preventing a condition characterized by formation of amyloid plaque and/or tau plaque, comprising: administering, to a patient in need thereof, an effective amount of sterubin.

In a generally applicable fourth aspect (i.e., independently combinable with any of the aspects or embodiments identified herein), a method is provided of supporting brain health or brain function, comprising: administering, to a patient in need thereof, an effective amount of sterubin.

In an embodiment of the second, third, or fourth aspect (i.e., independently combinable with any of the aspects or embodiments identified herein), the sterubin is administered in a form of a chewable tablet.

In an embodiment of the second, third, or fourth aspect (i.e., independently combinable with any of the aspects or embodiments identified herein), the sterubin is administered in a form of a spray for oral administration.

In an embodiment of the second, third, or fourth aspect (i.e., independently combinable with any of the aspects or embodiments identified herein), the sterubin is administered in a form adapted to be delivered to the patient by inhalation in a form of a vapor, a mist, or an aerosol.

In an embodiment of the second, third, or fourth aspect (i.e., independently combinable with any of the aspects or embodiments identified herein), the sterubin is administered in a form for administration at a dosage of 300 mg, in sublingual form for absorption under the tongue, wherein the form contains: 1) Sterubin-bio-concentrated, Yerba Santa (11.2 wt. %); 2) Gamma aminobutyric acid (10.7 wt. %); 3) tauroursodeoxycholic acid (10.7 wt. %); 4) Glutathione (9.7 wt. %); 5) Nicotinamide mononucleotide (9.5 wt. %); 6) Alpha-glyceryl phosphorylcholine (8.5 wt. %); 7) 5-hydroxytryptophan (5.5 wt. %); 8) Phosphatidylserine (4.8 wt. %); 9) Star Anis (2.5 wt. %); 10) Omega oil (11.5 wt. %); 11) Glycerin (11.4 wt. %); 12) Monk Fruit (2.8 wt. %); and 13) Magnesium Stearate (1.2 wt. %).

In an embodiment of the first aspect (i.e., independently combinable with any of the aspects or embodiments identified herein), the pharmaceutical composition or dietary supplement or health supplement or other physiologically-acceptable formulation further comprises glutathione.

In an embodiment of the first aspect (i.e., independently combinable with any of the aspects or embodiments identified herein), the pharmaceutical composition or dietary supplement or health supplement or other physiologically-acceptable formulation further comprises tauroursodeoxycholic acid.

In an embodiment of the second, third, or fourth aspect (i.e., independently combinable with any of the aspects or embodiments identified herein), the method further comprises administering glutathione.

In an embodiment of the second, third, or fourth aspect (i.e., independently combinable with any of the aspects or embodiments identified herein), the method further comprises administering tauroursodeoxycholic acid.

In a generally applicable fifth aspect (i.e., independently combinable with any of the aspects or embodiments identified herein), a composition substantially as presented herein is provided.

In a generally applicable sixth aspect (i.e., independently combinable with any of the aspects or embodiments identified herein), s method substantially as presented herein is provided.

Any of the features of an embodiment of aspects is applicable to all other aspects and embodiments identified herein. Moreover, any of the features of an embodiment is independently combinable, partly or wholly with other embodiments described herein in any way, e.g., one, two, or three or more embodiments may be combinable in whole or in part. Further, any of the features of an embodiment may be made optional to other aspects or embodiments. Any aspect or embodiment of a method can be performed using a composition of another aspect or embodiment, and any aspect or embodiment of a composition can be adapted to be used in a method of another aspect or embodiment.

BRIEF DESCRIPTION OF THE DRAWINGS

Further aspects of the present disclosure will be more readily appreciated upon review of the detailed description of the various disclosed embodiments, described below, when taken in conjunction with the accompanying FIGURES.

DETAILED DESCRIPTION OF THE EMBODIMENTS

The following description and examples illustrate an embodiment of the present invention in detail. Those of skill in the art will recognize that there are numerous variations and modifications of this invention that are encompassed by its scope. Accordingly, the description of an embodiment should not be deemed to limit the scope of the present invention.

Figure 1:
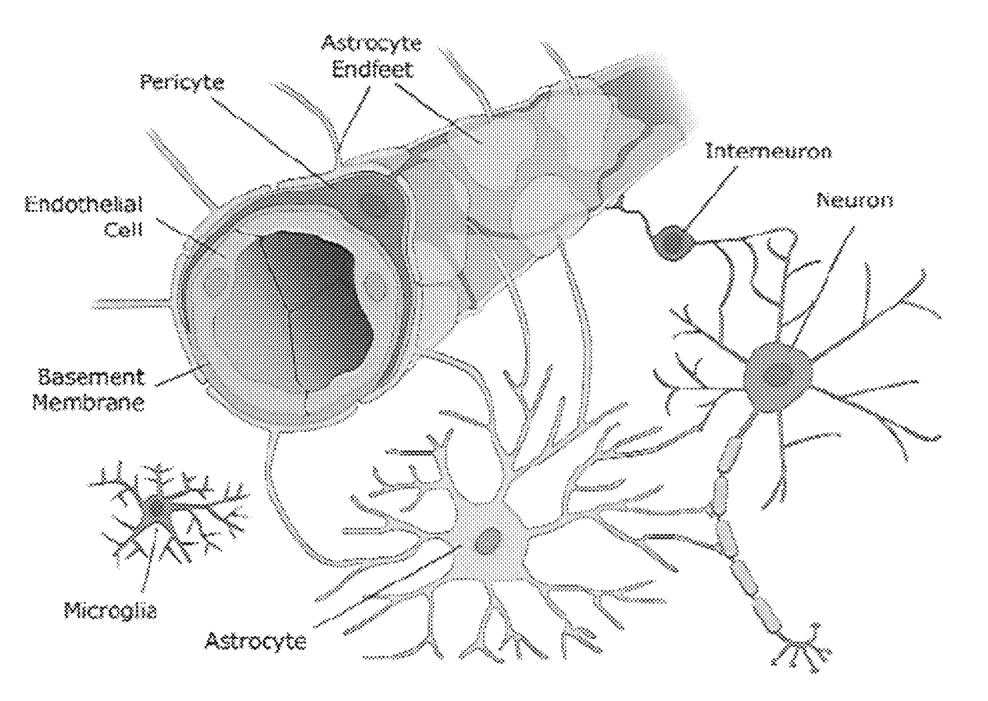
FIG. 1 is a drawing depicting the blood brain barrier (BBB) anatomy.

The blood brain barrier (BBB) anatomy consists of three complex, selectively permeable structures. The BBB structures have a combined cross section of ca 25 microns. The BBB is tasked with allowing fluids and nutrition to flow to the over 100 million neurites that compose the principal mass of this portion of the CNS network, which is the control center of life; but which is the primary defense against pathogens and harmful chemical which also flow within the micro environment of the body's blood supply.

Moving radially outward from the blood vessel plasma the three anatomical structure categories are:

BBB Structure #1 consisting of: a) the endothelial cells lining the blood vessels and capillaries feeding the blood micro environment to the brain and b) the tight junction between the endothelial cells.

BBB Structure #2 consisting of: a) the basal lamina, b) embedded pericyte cells and c) macrophage cells.

BBB Structure #3 consisting of: glia-astrocytes.

Briefly the functions of each category are as follows.

BBB Structure #1 a)

The endothelium is the inner-most layer of cells of all blood vessels. Endothelial cells are flattened and polygonal. Endothelial cells are polarized with their apical surface facing the lumen of vessels and the abluminal (basolateral of epithelial cells) facing the basement membrane. Because they make direct contact with blood, endothelial cells perform many essential functions:

Permeability: selective and adjustable barrier that allows rapid diffusion of gases and small metabolites but restricts the passage of proteins and cells.

Vascular control: sense local blood flow and regulate by inducing contraction or relaxation of underlying smooth muscle.

Haemostatic control: inhibit platelet aggregation and secrete components of clotting cascade (von Willebrand factor).

Immune response: recruit leukocytes to sites of infection or tissue damage and mediate entry into surrounding tissue.

Angiogenesis: initiate growth of new blood vessels.

BBB Structure #1 b)

Intercellular junctions mediate adhesion and communication between adjoining endothelial and epithelial cells. In the endothelium, junctional complexes comprise tight junctions, adherens junctions, and gap junctions. The expression and organization of these complexes depend on the type of vessels and the permeability requirements of perfused organs. Gap junctions are communication structures, which allow the passage of small molecular weight solutes between neighboring cells. Tight junctions serve the major functional purpose of providing a "barrier" and a "fence" within the membrane, by regulating paracellular permeability and maintaining cell polarity. Adherens junctions play an important role in contact inhibition of endothelial cell growth, paracellular permeability to circulating leukocytes and solutes. In addition, they are required for a correct organization of new vessels in angiogenesis. Extensive research in the past decade has identified several molecular components of the tight and adherens junctions, including integral membrane and intracellular proteins. These proteins interact both among themselves and with other molecules.

BBB Structure #2 a)

Basal laminas are specialized sheets of extracellular matrix that in epithelia underlie the epithelial cells and separate them from the adjoining stroma. They influence epithelial cell proliferation and differentiation and can selectively retard the passage of molecules from one side of a basal lamina to the other. Basal laminas are composed of a lattice-type network of type IV collagen intertwined with a network of laminin. This structure is stabilized by the binding of entactin/nidogen to the collagen and laminin. The heparan sulfate proteoglycan perlecan and other molecules are associated with the type IV collagen-laminin backbone. Importantly, basal laminas in different regions of the body differ in the ratio of all these components. Furthermore, each "component" is really a class of several components. Thus, each type IV collagen molecule is composed of three α chains, but to date, six different types of α chain (α1 to α6) have been discovered. Potentially, any combination of these might be present. Similarly, each laminin molecule is composed of one α (A in the old nomenclature), one β (B1 in the old nomenclature), and one γ (B2 in the old nomenclature) chain, yet five different α chains, three β chains, and three γ chains have been discovered. It is believed that the unique composition of each basal lamina contributes to its specific functional properties.

BBB Structure #2 b)

Pericytes are multi-functional cells embedded within the walls of capillaries throughout the body, including the brain. Pericytes were first identified in the 1870s, but little attention was paid to them during the following century. More recently, numerous vascular functions of pericytes have been identified including regulation of cerebral blood flow, maintenance of the blood-brain barrier (BBB), and control of vascular development and angiogenesis. Pericytes can also facilitate neuroinflammatory processes and possess stem cell-like properties. Pericytes form part of the neurovascular unit (NVU), a collection of cells that control interactions between neurons and the cerebral vasculature to meet the energy demands of the brain. Pericyte structure, expression profile, and function in the brain differ depending on their location along the vascular bed. Until recently, it has been difficult to accurately define the sub-types of pericytes, or to specifically target pericytes with pharmaceutical agents, but emerging techniques both in vitro and in vivo will improve investigation of pericytes and allow for the identification of their possible roles in diseases. Pericyte dysfunction is increasingly recognized as a contributor to the progression of vascular diseases such as stroke and neurodegenerative diseases such as Alzheimer's disease. The therapeutic potential of pericytes to repair cerebral blood vessels and promote angiogenesis due to their ability to behave like stem cells has recently been brought to light.

BBB Structure #2 c)

Macrophages are extraordinarily versatile cells. They are found in some guise in practically every tissue in the body, where they participate in an overwhelming array of biological processes, ranging from development, to bone remodeling and wound healing. However, it is as sentinels of the immune system that macrophages exploit their full functional repertoire; they detect, ingest and destroy infectious agents; they initiate T-cell responses by antigen presentation, and they act as effector cells for both humoral and cell-mediated immune responses. Because of their powerful and diverse effects, macrophage function is tightly regulated. Sometimes, these controls go awry, and macrophages become the etiological agents of a wide array of inflammatory diseases.

BBB Structure #3)

Glial cells, consisting of microglia, astrocytes, and oligodendrocyte lineage cells as their major components, constitute a large fraction of the mammalian brain. Originally considered as purely non-functional glue for neurons, decades of research have highlighted the importance as well as further functions of glial cells. Although many aspects of these cells are well characterized nowadays, the functions of the different glial populations in the brain under both physiological and pathological conditions remain, at least to a certain extent, unresolved. To tackle these important questions, a broad range of depletion approaches have been developed in which microglia, astrocytes, or oligodendrocyte lineage cells (i.e., NG2-glia and oligodendrocytes) are specifically ablated from the adult brain network with a subsequent analysis of the consequences. As the different glial populations are very heterogeneous, it is imperative to specifically ablate single cell populations instead of inducing cell death in all glial cells in general. Thanks to modern genetic manipulation methods, the approaches can now directly be targeted to the cell type of interest making the ablation more specific compared to general cell ablation approaches that have been used earlier on. In this review, we will give a detailed summary on different glial ablation studies, focusing on the adult mouse central nervous system and the functional readouts. We will also provide an outlook on how these approaches could be further exploited in the future.

Introduction

Glial cells were first identified by the 19th century's leading neuroscientists including Rudolf Virchow, Santiago Ramón y Cajal and Pío del Río-Hortega. At that time, glia were suggested to solely function as so-called "Nervenkitt" (the German word for nerve glue). This is also reflected in the name "glial cell" derived from the ancient Greek word "glía" meaning "glue" in English. With time, scientists started to speculate about additional possible roles of these cells. Although many studies have been performed to specify these further roles, the full properties of glial cells remain unresolved. Moreover, glial cells are anything but a minor cellular fraction, as they constitute—depending on the mammalian species—between 33 and 66% of the total brain mass (Azevedo, F. A. C., Carvalho, L. R. B., Grinberg, L. T., Farfel, J. M., Ferretti, R. E. L., Leite, R. E. P., et al. (2009). Equal numbers of neuronal and nonneuronal cells make the human brain an isometrically scaled-up primate brain. *J. Comp. Neurol.* 513, 532-541. doi: 10.1002/cne.21974; Herculano-Houzel, S. (2014). The glia/neuron ratio: how it varies uniformly across brain structures and species and what that means for brain physiology and evolution. *Glia* 62, 1377-1391. doi: 10.1002/glia.22683). Recent findings have made it clear that glial cells are more than just mere "Nervenkitt". The total glial cell population can be subdivided into four major groups: (1) microglia, (2) astrocytes, (3) oligodendrocytes, and (4) their progenitors NG2-glia. This review will focus on the research of the past decades addressing the role of these four major glial cell types in regard to the function of the adult brain.

The analysis of cellular function can be addressed through a range of different experimental measures. One common technique involves the depletion of mature brain cells that are already integrated in an established network in vivo. During the last two decades, various ways have been developed to achieve this goal. Initially, cytotoxic substances, such as ethidium bromide (EtBr) that are lethal for cells in general (including neurons) were used (Yajima, K., and Suzuki, K. (1979). Demyelination and remyelination in the rat central nervous system following ethidium bromide injection. *Lab. Invest.* 41, 385-392). To specifically target and subsequently ablate cycling cells, the application of high doses of X-irradiation (Kalderon, N., and Fuks, Z. (1996). Severed corticospinal axons recover electrophysiologic control of muscle activity after x-ray therapy in lesioned adult spinal cord. *Proc. Natl. Acad. Sci. U.S.A.* 93, 11185-11190; Chari, D. M., and Blakemore, W. F. (2002). Efficient recolonisation of progenitor-depleted areas of the CNS by adult oligodendrocyte progenitor cells. *Glia* 37, 307-313. doi: 10.1002/glia.10038.abs) or of the mitotic blocker arabinofuranosyl cytidine (AraC) (Doetsch, F., Garcia-Verdugo, J. M., and Alvarez-Buylla, A. (1999). Regeneration of a germinal layer in the adult mammalian brain. *Proc. Natl. Acad. Sci. U.S.A.* 96, 11619-11624. doi: 10.1073/pnas.96.20.11619) to the tissue of interest has also proven to be successful. These general ablation approaches, which are still in use today, were likely favored due to the simplicity of application and due to the lack of more specific alternatives. X-irradiation as well as the application of AraC is not cell type specific, as all cycling cells in the area (X-irradiation) or tissue (AraC) of interest undergo induced cell death. Therefore these approaches are not ideal to identify the function of a specific cell type. The same is true for EtBr, as it induces general unrepairable DNA damage leading to cell death (Yajima, K., and Suzuki, K. (1979). Demyelination and remyelination in the rat central nervous system following ethidium bromide injection. *Lab. Invest.* 41, 385-392; Johnson, I. M., Kumar, S. G., and Malathi, R. (2003). De-intercalation of ethidium bromide and acridine orange by xanthine derivatives and their modulatory effect on anticancer agents: a study of DNA-directed toxicity enlightened by time correlated single photon counting. *J. Biomol. Struct. Dyn.* 20, 677-686. doi: 10.1080/07391102.2003.10506884). The use of such general approaches has decreased, as drugs can have effects in other tissues that lead to secondary damage or even changes in the cells of interest. As genetic manipulation has become easier and more accessible within the recent years, cell ablation techniques have also improved. Nowadays, most ablation approaches make use of a cell type or a region-specific promoter that is coupled with a "suicide" gene, resulting in depletion of distinct cell types. Suicide genes typically encode either a toxin, an enzyme that converts a pro-drug into a toxic agent, or an essential protein for the specific cell type leading to apoptotic cell death specifically in the cells of interest. The main advantage of these approaches is that they have few side effects for surrounding cells or other tissues.

Application of these ablation methods have already helped us to better understand the functions of all four major glial cell types in the adult brain. This review will summarize and discuss the major findings of ablation studies performed during the last few decades.

Microglia

Microglia Ablation Under Healthy Conditions

In a very simplified view, microglia are the immunocompetent and phagocytic cells of the nervous system. Although they are part of the brain's glia, they do not originate from the ectodermal tissue like all other glial cells, but from yolk-sac progenitors that only populate the brain during development (reviewed in Kim, S. U., and de Vellis, J. (2005). Microglia in health and disease. *J. Neurosci. Res.* 81, 302-313. doi: 10.1002/jnr.20562; Kettenmann, H., Hanisch, U.-K., Noda, M., and Verkhratsky, A. (2011). Physiology of microglia. *Physiol. Rev.* 91, 461-553. doi: 10.1152/physrev.00011.2010). Microglia have been shown to cover a huge volume of the adult brain parenchyma, with individual non-overlapping domains constantly sensing the environment through rapid movements of their fine filopodia, which react to any kind of insult (Nimmerjahn, A., Kirchhoff, F., and Helmchen, F. (2005). Resting microglial cells are highly dynamic surveillants of brain parenchyma in vivo. *Science* 308, 1314-1318. doi: 10.1126/science.1110647; Cronk, J. C., and Kipnis, J. (2013). Microglia—the brain's busy bees. *F1000Prime Rep.* 5:53. doi: 10.12703/P5-53). As microglia in the brain have the same origin and express many common cellular markers with peripheral macrophages/monocytes, it has proven difficult to only ablate one but not the other cell type (Silver, J., Schwab, M. E., and Popovich, P. G. (2015). Central nervous system regenerative failure: role of oligodendrocytes, astrocytes, and microglia. *Cold Spring Harb. Perspect. Biol.* 7:a020602. doi: 10.1101/cshperspect.a020602). Additionally, macrophages are able to invade the brain upon injury or any other disturbance of the blood brain barrier (BBB), meaning that the roles of microglia and macrophages have been difficult to disentangle (Pineau, I., Sun, L., Bastien, D., and Lacroix, S. (2010). Astrocytes initiate inflammation in the injured mouse spinal cord by promoting the entry of neutrophils and inflammatory monocytes in an IL-1 receptor/MyD88-dependent fashion. *Brain Behav. Immun.* 24, 540-553. doi: 10.1016/j.bbi.2009.11.007). Several of the microglia ablation studies tried to address the issue of how these cells maintain their homeostasis in the adult healthy brain. Microglia could either derive from a brain intrinsic stem cell source or from a peripheral derived progenitor originating from the same developmental source that infiltrates the brain at some stage and contributes to the microglia population. From these studies, it seemed that at least under physiological conditions the two populations remain separated (see below). In addition, there is the question about other roles played by microglia besides surveying the healthy tissue, as microglia have been shown to be major players in synaptic pruning during development (reviewed in Wu, Y., Dissing-Olesen, L., MacVicar, B. A., and Stevens, B. (2015). Microglia: dynamic mediators of synapse development and plasticity.

*Trends Immunol.* 36, 605-613. doi: 10.1016/j.it.2015.08.008) and in synaptic modulation both in normal as well as under pathological conditions (Bessis, A., Béchade, C., Bernard, D., and Roumier, A. (2007). Microglial control of neuronal death and synaptic properties. *Glia* 55, 233-238. doi: 10.1002/glia.20459; Hong, S., Beja-Glasser, V. F., Nfonoyim, B. M., Frouin, A., Li, S., Ramakrishnan, S., et al. (2016a). Complement and microglia mediate early synapse loss in Alzheimer mouse models. *Science* 352, 712-716. doi: 10.1126/science.aad8373; Hong, S., Dissing-Olesen, L., and Stevens, B. (2016b). New insights on the role of microglia in synaptic pruning in health and disease. *Curr. Opin. Neurobiol.* 36, 128-134. doi: 10.1016/j.conb.2015.12.004; Vasek, M. J., Garber, C., Dorsey, D., Durrant, D. M., Bollman, B., Soung, A., et al. (2016). A complement-microglial axis drives synapse loss during virus-induced memory impairment. *Nature* 534, 538-543. doi: 10.1038/nature18283). Further microglia ablation studies could therefore provide a potential tool to describe yet unknown microglia-associated functions in adult brain physiology.

Although several studies have depleted myeloid cells—including microglia—during development by inserting deleterious mutations in macrophage-specific genes (reviewed in Waisman, A., Ginhoux, F., Greter, M., and Bruttger, J. (2015). Homeostasis of microglia in the adult brain: review of novel microglia depletion systems. *Trends Immunol.* 36, 625-636. doi: 10.1016/j.it.2015.08.005), this review will focus only on microglia ablation studies performed in the adult brain.

To successfully ablate adult microglia, pharmacological and genetic strategies have been developed. As a pharmacological approach, the use of the systemically administered drug PLX3397, which specifically targets Colony-stimulating factor 1 receptor (CSF-1R) signaling, has been well established. CSF-1R is uniquely expressed on myeloid cells including brain resident microglia, making only these cells susceptible to death (Elmore, M. R., Najafi, A. R., Koike, M. A., Dagher, N. N., Spangenberg, E. E., Rice, R. A., et al. (2014). Colony-stimulating factor 1 receptor signaling is necessary for microglia viability, unmasking a microglia progenitor cell in the adult brain. *Neuron* 82, 380-397. doi: 10.1016/j.neuron.2014.02.040). The use of clodronate liposomes (CLs) is a second pharmacological way to specifically deplete phagocytic cells, including microglia (van Rooijen, N., Kors, N., vd Ende, M., and Dijkstra, C. D. (1990). Depletion and repopulation of macrophages in spleen and liver of rat after intravenous treatment with liposome-encapsulated dichloromethylene diphosphonate. *Cell Tissue Res.* 260, 215-222. doi: 10.1007/BF00318625). After the phagocytic cells take up the liposomal particles and release the encapsulated, toxic clodronate they undergo apoptosis. As a genetic approach, the diphtheria toxin (DT) or its subunit A (DTA), originally derived from the bacterium *Corynebacterium diphtheriae*, is a widely used suicide gene that has already been applied in ablation approaches. Its mode of action is the cytosolic inhibition of cellular protein synthesis, leading to cell death (Honjo, T., Nishizuka, Y., and Hayaishi, O. (1968). Diphtheria toxin-dependent adenosine diphosphate ribosylation of aminoacyl transferase II and inhibition of protein synthesis. *J. Biol. Chem.* 243, 3553-3555). The DT-dependent ablation system can be used in two ways: (1) direct tamoxifen-inducible expression of the DT(A) in the target cells or (2) cell type-specific expression of the diphtheria toxin receptor (DTR) in combination with the systemic application of DT(A), such that only cells carrying the receptor are susceptible to death. Independent of methodology (pharmacological or genetic), all of these approaches achieve fast and robust microglia death in the brain, ranging from 80 to >99% depending on the treatment and the region of interest (Parkhurst, C. N., Yang, G., Ninan, I., Savas, J. N., Yates, J. R., Lafaille, J. J., et al. (2013). Microglia promote learning-dependent synapse formation through brain-derived neurotrophic factor. *Cell* 155, 1596-1609. doi: 10.1016/j.cell.2013.11.030; Elmore, M. R., Najafi, A. R., Koike, M. A., Dagher, N. N., Spangenberg, E. E., Rice, R. A., et al. (2014). Colony-stimulating factor 1 receptor signaling is necessary for microglia viability, unmasking a microglia progenitor cell in the adult brain. *Neuron* 82, 380-397. doi: 10.1016/j.neuron.2014.02.040; Elmore, M. R., Lee, R. J., West, B. L., and Green, K. N. (2015). Characterizing newly repopulated microglia in the adult mouse: impacts on animal behavior, cell morphology, and neuroinflammation. *PLoS ONE* 10:e0122912. doi: 10.1371/journal.pone.0122912; Bruttger, J., Karram, K., Wörtge, S., Regen, T., Marini, F., Hoppmann, N., et al. (2015). Genetic cell ablation reveals clusters of local self-renewing microglia in the mammalian central nervous system. *Immunity* 43, 92-106. doi: 10.1016/j.immuni.2015.06.012; Torres, L., Danver, J., Ji, K., Miyauchi, J. T., Chen, D., Anderson, M. E., et al. (2016). Dynamic microglial modulation of spatial learning and social behavior. *Brain Behav. Immun.* 55, 6-16. doi: 10.1016/j.bbi.2015.09.001).

Components of the Physiologically-Acceptable Formulation

The formulations of the various embodiments can comprise one or more of the following components. These formulations can support brain health and brain function, support or improve mood or energy levels, as well as treat, prevent, or ameliorate one or more of the conditions identified herein.

1) Sterubin-bio-concentrated, Yerba Santa—See, e.g., Fischer, W., Currais, A., Liang, Z., Pinto, A. and Maher, P. (Salk Institute) Old age-associated phenotypic screening for Alzheimer's disease drug candidates identifies sterubin as a potent neuroprotective compound from Yerba Santa. Redox Biol. 2019 February; 21:101089.

2) GABA—Gamma aminobutyric acid (GABA) is a naturally occurring amino acid that works as a neurotransmitter in the brain.

3) TUDCA—Tauroursodeoxycholic acid (TUDCA) is an enzyme that is naturally produced in the liver. It is a small molecule that is being explored for its potential as a treatment for central nervous system (CNS) disorders such as Alzheimer's, Parkinson's and amyotrophic lateral sclerosis (ALS). Research has shown that TUDCA can decrease nerve cell death, a hallmark of ALS, through its ability to act as an antioxidant that prevents toxic reactive oxygen species from accumulating inside cells. The molecule also has the ability to control immune function.

4) Glutathione—Glutathione is the master, anti-inflammatory, substance made from the amino acids glycine, cysteine, and glutamic acid. It is a tripeptide produced naturally by the liver and is involved in many processes in the body, including tissue building and repair, making chemicals and proteins needed in the body, and for the immune system. Supporting maintenance of healthy glutathione levels is therefore desirable in supporting health, especially brain health, hence the inclusion of glutathione in certain formulations disclosed herein. Glutamate, derived from glutathione, is one of five key brain neurotransmitter molecules. The glutathione, a large molecule tripeptide which will not pass the BBB element, it can be considered an engineered, ligand structured, chain consisting of the three primary, research established protein building blocks glycine, cysteine, and glutamic acid. Alone, glycine, cysteine, and glutamic acid will not have the proper polarity to pass the BBB. However, in a form of glutathione and immersed in the transfer platform of the other components, they will enter the cell structure and convert to glycine, cysteine, and glutamic acid. Plasma levels of glutathione rise in direct response to oral consumption of these amino acids under certain circumstances, therefore, inclusion of glycine, cysteine, and glutamic acid in the formulations of the embodiments may support glutathione levels as well, e.g., to support cellular formation of glutathione. Accordingly, certain of the formulations as described herein can contain glycine, cysteine, and glutamic acid in combination with glutathione, or glutathione alone, or the combination of glycine, cysteine, and glutamic acid in the absence of glutathione. Such components can provide support to the healthy, neuro-physiology re-structuring process concurrent to the plaque and invading micro-biology scouring effect of the combination of sterubin and TUDCA.

5) NMN—Nicotinamide mononucleotide (NMN) is a molecule naturally occurring in all life forms. At the molecular level, it is a ribo-nucleotide, which is a basic structural unit of the nucleic acid RNA. Structurally, the molecule is composed of a nicotinamide group, a ribose and a phosphate group. NMN is the direct precursor of the essential molecule nicotinamide adenine dinucleotide (NAD+) and is considered a key component to increase NAD+ levels in cells.

6) A-GPC—Alpha-glyceryl phosphorylcholine (Alpha-GPC) is a natural physiological precursor to acetyl-choline, a neurotransmitter that is involved in memory and other cognitive functions.

7) 5 HTP—5-hydroxytryptophan (5-HTP) is a chemical that the body makes from tryptophan (an essential amino acid that one gets from food). After tryptophan is converted into 5-HTP, the chemical is changed into another chemical called serotonin (a neurotransmitter that relays signals between brain cells). 5-HTP dietary supplements help raise serotonin levels in the brain. Since serotonin helps regulate mood and behavior, 5-HTP may have a positive effect on sleep, mood, anxiety, appetite, and pain sensation.

8) Phosphatidylserine—Phosphatidylserine is a fatty substance produced in the body that covers and protects every cell in the body, and is involved in the clotting function of the body. It is particularly vital for the proper functioning of nerve cells within the brain, helping to transmit messages between them.

9) Star Anis—A spice, commonly called star anise, has been shown to possess potent antimicrobial properties. It is a fruit harvested from *Illicium verum*, a medium-sized evergreen tree native to northeast Vietnam and southwest China.

10) Omega oil—Omega-3s are nutrients one gets from food (or supplements) that help build and maintain a healthy body. The three main omega-3 fatty acids are alpha-linolenic acid (ALA), eicosapentaenoic acid (EPA), and docosahexaenoic acid (DHA).

11) Glycerin—Glycerin is a simple polyol-compound. It is a colorless, odorless, viscous liquid that is sweet-tasting and non-toxic. The glycerol backbone is found in most plants in the form of glycerides. Due to having antimicrobial and antiviral properties it is widely used in FDA approved supplements and wound and burn treatments.

12) Monk Fruit—Monk fruit (sweetener), grown in a pesticide-free, high altitude mountain setting is considered one of the highest levels of healing herbs in Eastern medicine and has been used since its discovery to treat all kinds of ailments.

13) Mag Stearate (trace)—Fatty acids reacted with a source of magnesium, such as magnesium oxide, to form magnesium salts of the fatty acids. It is FDA approved for use in all forms of drugs and supplements and has been safely used in foods for nearly a century to improve mixing and digestion.

The foregoing substances are generally recognized as safe (GRAS), and can be provided in natural or synthetic form, in either unpurified form or in any suitable degree of purity (e.g., as an extract or concentrate).

Definitions

The term "alcohol" as used herein is a broad term, and is to be given its ordinary and customary meaning to a person of ordinary skill in the art (and is not to be limited to a special or customized meaning), and refers without limitation to any compound as described herein incorporating one or more hydroxy groups, or being substituted by or functionalized to include one or more hydroxy groups.

The term "derivative" as used herein is a broad term, and is to be given its ordinary and customary meaning to a person of ordinary skill in the art (and is not to be limited to a special or customized meaning), and refers without limitation to any compound as described herein incorporating one or more derivative groups, or being substituted by or functionalized to include one or more derivative groups. Derivatives include but are not limited to esters, amides, anhydrides, acid halides, thioesters, and phosphates.

The term "hydrocarbon" as used herein is a broad term, and is to be given its ordinary and customary meaning to a person of ordinary skill in the art (and is not to be limited to a special or customized meaning), and refers without limitation to any moiety comprising only carbon and hydrogen atoms. A functionalized or substituted hydrocarbon moiety has one or more substituents as described elsewhere herein.

The term "lipid" as used herein is a broad term, and is to be given its ordinary and customary meaning to a person of ordinary skill in the art (and is not to be limited to a special or customized meaning), and refers without limitation to saturated and unsaturated oils and waxes, derivatives, amides, glycerides, fatty acids, fatty alcohols, sterol and sterol derivatives, tocopherols, carotenoids, among others.

The terms "pharmaceutically acceptable" as used herein is a broad term, and is to be given its ordinary and customary meaning to a person of ordinary skill in the art (and is not to be limited to a special or customized meaning), and refers without limitation to those compounds, materials, compositions, and/or dosage forms which are, within the scope of sound medical judgment, suitable for contact with the tissues of and/or for consumption by human beings and animals without excessive toxicity, irritation, allergic response, or other problem complications commensurate with a reasonable risk/benefit ratio.

The terms "pharmaceutically acceptable salts" and "a pharmaceutically acceptable salt thereof" as used herein are broad terms, and are to be given their ordinary and customary meaning to a person of ordinary skill in the art (and is not to be limited to a special or customized meaning), and refer without limitation to salts prepared from pharmaceutically acceptable, non-toxic acids or bases. Suitable pharmaceutically acceptable salts include metallic salts, e.g., salts of aluminum, zinc, alkali metal salts such as lithium, sodium, and potassium salts, alkaline earth metal salts such as calcium and magnesium salts; organic salts, e.g., salts of lysine, N,N'-dibenzylethylenediamine, chloroprocaine, choline, diethanolamine, ethylenediamine, meglumine (N-methylglucamine), procaine, and tris; salts of free acids and bases; inorganic salts, e.g., sulfate, hydrochloride, and hydrobromide; and other salts which are currently in widespread pharmaceutical use and are listed in sources well known to those of skill in the art, such as, for example, The Merck Index. Any suitable constituent can be selected to make a salt of the therapeutic agents discussed herein, provided that it is non-toxic and does not substantially interfere with the desired activity. In addition to salts, pharmaceutically acceptable precursors and derivatives of the compounds can be employed. Pharmaceutically acceptable amides, lower alkyl derivatives, and protected derivatives can also be suitable for use in compositions and methods of preferred embodiments. While it may be possible to administer the compounds of the preferred embodiments in the form of pharmaceutically acceptable salts, it is generally preferred to administer the compounds in neutral form.

The term "pharmaceutical composition" as used herein is a broad term, and is to be given its ordinary and customary meaning to a person of ordinary skill in the art (and is not to be limited to a special or customized meaning), and refers without limitation to a mixture of one or more compounds disclosed herein with other chemical components, such as diluents or carriers. The pharmaceutical composition facilitates administration of the compound to an organism. Pharmaceutical compositions can also be obtained by reacting compounds with inorganic or organic acids or bases. Pharmaceutical compositions will generally be tailored to the specific intended route of administration.

As used herein, a "carrier" as used herein is a broad term, and is to be given its ordinary and customary meaning to a person of ordinary skill in the art (and is not to be limited to a special or customized meaning), and refers without limitation to a compound that facilitates the incorporation of a compound into cells or tissues. For example, without limitation, dimethyl sulfoxide (DMSO) is a commonly utilized carrier that facilitates the uptake of many organic compounds into cells or tissues of a subject. Water, saline solution, ethanol, and mineral oil are also carriers employed in certain pharmaceutical compositions.

As used herein, a "diluent" as used herein is a broad term, and is to be given its ordinary and customary meaning to a person of ordinary skill in the art (and is not to be limited to a special or customized meaning), and refers without limitation to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood. When a tincture or other liquid form is prepared, animal, vegetable oils, or mineral oils suitable for human consumption can advantageously be employed as diluents. For example, suitable vegetable oils include but are not limited to olive oil, coconut oil, MCT (mixed chain triglycerides derived from coconut oil), and avocado oil.

As used herein, an "excipient" as used herein is a broad term, and is to be given its ordinary and customary meaning to a person of ordinary skill in the art (and is not to be limited to a special or customized meaning), and refers without limitation to a substance that is added to a pharmaceutical composition to provide, without limitation, bulk, consistency, stability, binding ability, lubrication, disintegrating ability etc., to the composition. A "diluent" is a type of excipient.

As used herein, a "subject" or "patient" as used herein is a broad term, and is to be given its ordinary and customary meaning to a person of ordinary skill in the art (and is not to be limited to a special or customized meaning), and refers without limitation to an animal that is the object of support, treatment, observation, or experiment. "Animal" includes cold- and warm-blooded vertebrates and invertebrates such as fish, shellfish, reptiles, and, in particular, mammals. "Mammal" includes, without limitation, dolphins, mice, rats, rabbits, guinea pigs, dogs, cats, sheep, goats, cows, horses, primates, such as monkeys, chimpanzees, and apes, and, in particular, humans. In some embodiments, the subject is human.

As used herein, the terms "treating," "treatment," "therapeutic," or "therapy" are broad terms, and are to be given their ordinary and customary meaning (and are not to be limited to a special or customized meaning) and, without limitation, do not necessarily mean total cure or abolition of the disease or condition. Any alleviation of any undesired markers, signs or symptoms of a disease or condition, to any extent, can be considered treatment and/or therapy. Furthermore, treatment may include acts that may worsen the patient's overall feeling of well-being or appearance.

The terms "therapeutically effective amount" and "effective amount" as used herein are broad terms, and are to be given its ordinary and customary meaning to a person of ordinary skill in the art (and are not to be limited to a special or customized meaning), and are used without limitation to indicate an amount of an active compound, or pharmaceutical agent, that elicits the biological or medicinal response indicated. For example, a therapeutically effective amount of compound can be the amount needed to prevent, alleviate or ameliorate markers or symptoms of a condition or prolong the survival of the subject being treated. This response may occur in a tissue, system, animal or human and includes alleviation of the signs or symptoms of the disease being treated. Determination of a therapeutically effective amount is well within the capability of those skilled in the art, in view of the disclosure provided herein. The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

The term "solvents" as used herein is a broad term, and is to be given its ordinary and customary meaning to a person of ordinary skill in the art (and is not to be limited to a special or customized meaning), and refers without limitation to compounds with some characteristics of solvency for other compounds or means, that can be polar or nonpolar, linear or branched, cyclic or aliphatic, aromatic, naphthenic and that includes but is not limited to: alcohols, derivatives, diesters, ketones, acetates, terpenes, sulfoxides, glycols, paraffins, hydrocarbons, anhydrides, heterocyclics, among others.

Pharmaceutical Compositions

Compositions including sterubin are provided, optionally with least one excipient. When made bio-available, numerous clinical studies support the efficacy of sterubin for treatment of central nervous system diseases such as Alzheimer's, Parkinson's and Multiple Sclerosis. The compositions can be advantageously administered in unit dosage form as an oral form, but other routes of administration, e.g., through inhalation (e.g., as a vapor, a mist, or an aerosol), are also contemplated. Delivery devices for inhalable forms include inhalers, humidifiers, and the like.

The components of the composition are readily available through conventional sources, and the compositions can offer help to those afflicted by central nervous system diseases.

The compositions described herein can be administered by themselves to a subject, or in compositions where they are mixed with other active agents, as in combination therapy, or with carriers, diluents, excipients or combinations thereof. Formulation is dependent upon the route of administration chosen. Techniques for formulation and administration of the compounds described herein are known to those skilled in the art (see, e.g., "Remington: The Science and Practice of Pharmacy", Lippincott Williams & Wilkins; 20th edition (Jun. 1, 2003) and "Remington's Pharmaceutical Sciences," Mack Pub. Co.; 18th and 19th editions (December 1985, and June 1990, respectively).

The compositions disclosed herein may be manufactured by a process that is itself known, e.g., by means of conventional mixing, dissolving, emulsifying, or extracting processes. Many of the compounds used in the pharmaceutical combinations disclosed herein may be provided as salts with pharmaceutically acceptable counterions.

Multiple techniques of administering pharmaceutical compositions exist in the art including, but not limited to, oral, rectal, topical, aerosol, injection and parenteral delivery, including intramuscular, subcutaneous, intravenous, intramedullary injections, intrathecal, direct intraventricular, intraperitoneal, intranasal and intraocular injections. Contemplated herein are any methods suitable for administering the composition (see, e.g., "Remington: The Science and Practice of Pharmacy", Lippincott Williams & Wilkins; 20th edition (Jun. 1, 2003) and "Remington's Pharmaceutical Sciences," Mack Pub. Co.; 18th and 19th editions (December 1985, and June 1990, respectively).

In practice, the sterubin may be combined as an active ingredient in intimate admixture with a pharmaceutical carrier according to conventional pharmaceutical compounding techniques. The carrier can take a wide variety of forms depending on the form of preparation desired for administration. Thus, the compositions provided herein can be presented as discrete units suitable for oral administration (e.g., unit dosage form tablets or capsules) or pulmonary administration such as vials containing a predetermined amount of the active ingredients. Further, the compositions can be presented as solids, powders, aqueous or nonaqueous solutions, as emulsions, or on or in a carrier as employed for providing a pharmaceutical composition. In addition to the common dosage forms set out above, the compounds provided herein, or pharmaceutically acceptable salts or derivatives thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both.

The compositions can be provided via a humidifier (e.g., an ultrasonic, mist, or vaporizer humidifier) as are commonly available over-the-counter. Other devices for administering include inhalers. The most common type of inhaler is the pressurized metered-dose inhaler (MDI) which is made up of 3 standard components—a metal canister, plastic actuator, and a metering valve. In MDIs, medication is typically stored in solution in a pressurized canister that contains a propellant, although it may also be a suspension. The MDI canister is attached to a plastic, hand-operated actuator. On activation, the metered-dose inhaler releases a fixed dose of medication in aerosol form. The correct procedure for using an MDI is to first fully exhale, place the mouth-piece of the device into the mouth, and having just started to inhale at a moderate rate, depress the canister to release the medicine. The aerosolized medication is drawn into the lungs by continuing to inhale deeply before holding the breath for 10 seconds to allow the aerosol to settle onto the walls of the bronchitis and other airways of the lung. Dry powder inhalers (DPI) release a metered or device-measured dose of powdered medication that is inhaled through a DPI device. Nebulizers supply the medication as an aerosol created from an aqueous formulation. Nasal inhalers deliver drugs to the upper respiratory tract. Propellants for inhalers include hydrofluoroalkane (HFA).

The pharmaceutical compositions contain sterubin in an amount effective for the desired therapeutic effect. In some embodiments, the compositions are provided in a carrier (e.g., a solid excipient, or glycerin and water) at a concentration of 0.01% to 10% by weight of sterubin. Depending upon the mode of delivery, higher or lower concentrations may be employed. The composition can be provided in a unit dosage form and comprise from about 0.1 mg or less to about 5000 mg or more of sterubin per unit dosage form. Such dosage forms may be provided in a ready to use form (e.g., tablet or capsule), or can be reconstituted in a suitable carrier fluid for delivery via aerosol, mist, vapor, or the like for inhalation administration.

Compositions provided herein can be prepared as solutions or suspensions of sterubin in water or oil or other liquid carrier. A suitable surfactant can be included such as, for example, hydroxypropylcellulose. Dispersions can also be prepared in glycerol, liquid polyethylene glycols, and mixtures thereof in oils. Further, a preservative can be included to, for example, prevent the detrimental growth of microorganisms.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Compositions containing a compound provided herein, or pharmaceutically acceptable salt or derivative thereof, can also be prepared in powder or liquid concentrate form for dilution.

The sterubin may be present in a single formulation or in multiple formulations provided together with other active ingredient(s), or may be unformulated. In some embodiments, sterubin can be administered with one or more additional agents together in a single composition. In a further embodiment, the sterubin compositions and other conventional therapeutics employed for treatment of central nervous system conditions are co-packaged in a kit. For example, a drug manufacturer, a drug reseller, a physician, a compounding shop, or a pharmacist can provide a kit comprising sterubin and other pharmaceutical agents for delivery to a patient.

Some embodiments described herein relate to a composition, which can include a therapeutically effective amount of sterubin. The pharmaceutical composition can include sterubin in, for example, >0.001%, ≥0.01%, ≥1%, ≥2%, ≥3%, ≥4%, ≥5%, ≥6%, ≥7%, ≥8%, ≥9%, ≥10%, ≥20%, or more of the composition. The pharmaceutical composition can include sterubin in, for example, 0.1% or less to 10% or more, for example, 0.1% to 10%, or 0.5% to 5% or 1% to 3% of the composition.

Ingestible and Non-Ingestible Compositions

Some embodiments described herein relate to a composition, which can include an effective amount of sterubin. In addition to pharmaceutical compositions, also contemplated are ingestible and non-ingestible compositions such as dietary supplements, foodstuffs, and similar compositions. Foodstuffs and other comestibles including the compositions disclosed herein are provided, wherein the foodstuff has been fortified (e.g., enriched or concentrated) or additized with sterubin. The component(s) may be added to foodstuffs for consumption by a subject. The component(s) may be integrated into one or more ingredients of a foodstuff. The component(s) may be prepared as an ingredient, or may be unprepared. The compound, or preparation including the compound, may be added prior to preparation, during preparation, or following preparation. Preparation may without limitation include cooking, mixing, flavoring, seasoning, blending, boiling, frying, baking, or other processes known in the art. Fortification is preferably at a level so as to provide a therapeutic or an effective dosage of the component(s) as described elsewhere herein; however, beneficial effects may also be obtained at amounts below such dosages.

The component(s) may be present as a constituent in foodstuffs by operation of processes known in nature, for example, by altering the metabolic processes of a plant, animal, bacteria, or fungus. Genetic alteration of a plant, animal, bacteria, or fungus to increase the concentration of sterubin is contemplated. By way of example, sterubin can be present in the foodstuff in a concentration of at least about 0.01%, at least about 0.1%, at least about 1%, at least about 2%, at least about 3%, at least about 4%, at least about 5%, at least about 6%, at least about 7%, at least about 8%, at least about 9%, at least about 10%, at least about 20%, at least about 30%, at least about 40%, at least about 50%, or higher, for example, 1% to 2% or 3% or 4% or 5% or 6% or 7% or 8% or 9% or 10% or 20% or 30% or 40% or 50%, e.g., from about 0.01% to about 50%, e.g., from about 0.1% to about 20%, e.g., from about 1% to about 15%, e.g., from about 1% to about 10% e.g., from about 1% to about 5%.

As used herein, an "ingestible composition" includes any composition that, either alone or together with another substance, is suitable to be taken by mouth whether intended for consumption or not. The ingestible composition includes both "food or beverage products" and "non-edible products". By "Food or beverage products", it is meant any edible product intended for consumption by humans or animals, including solids, semi-solids, or liquids (e.g., beverages) and includes functional food products (e.g., any fresh or processed food claimed to have a health-promoting and/or disease-preventing properties beyond the basic nutritional function of supplying nutrients) as well as dietary supplements in a unit dosage form. The terms "non-food or beverage products" or "noncomestible composition" or "noningestible composition" includes any product or composition that can be taken into the mouth by humans or animals for purposes other than consumption or as food or beverage. For example, the non-food or beverage product or noncomestible composition can include supplements, nutraceuticals, pharmaceuticals, natural products, prescribed drugs, over the counter medications, or, e.g., sterubin as described herein, for delivery to a human or other animal, using a delivery device such as, e.g., oral care products such as dentifrices and mouthwashes, and chewing gum.

The sterubin can be used in the manufacture of chewing gum, lozenges, candies, mints, powders or liquids suitable for reconstitution into a beverage or for addition to a foodstuff, sublingual tablets or lozenges adapted to be chewed, or to dissolve when placed under the tongue, sprayable liquid forms, capsules, or the like.

Indications

Provided herein are compositions and methods for to positively mitigating the progression of central nervous system diseases such as dementia (e.g., Lewy Body Dementia or Alzheimer's Dementia), Parkinson's Disease, and Multiple Sclerosis, or of diseases characterized by amyloid plaque and/or tau plaque. These conditions are treated by administration of sterubin in a suitable carrier.

As is readily apparent to one skilled in the art, the useful in vivo dosage to be administered and the particular mode of administration will vary depending upon the age, weight, the severity of the condition, and mammalian species treated, the particular forms of the various components employed, and the specific use for which these components are employed. The determination of effective dosage levels, that is the dosage levels necessary to achieve the desired result, can be accomplished by one skilled in the art using routine methods, for example, in vivo studies. Reference may be made to, for example, "Estimating the Maximum Safe Starting Dose in Initial Clinical Trials for Therapeutics in Adult Healthy Volunteers," U.S. Food and Drug Administration, July 2005.

In some embodiments, a method provided herein may comprise administering a therapeutically effective amount of a composition provided herein.

The dosage may vary broadly, depending upon the desired effects and the therapeutic indication. Alternatively, dosages may be based and calculated upon the surface area or weight of the patient, as understood by those of skill in the art. The exact dosage is determined on a case-by-case basis, or, in some cases, is left to the informed discretion of the subject. The daily dosage regimen for an adult human patient may be, for example, a dose of sterubin of from about 0.01 mg to about 10000 mg, from about 1 mg to about 5000 mg, from about 5 mg to about 2000 mg, from about 10 mg to about 1000 mg, or from about 50 mg to about 500 mg. The dosage may be adjusted according to the body mass of the subject, for example, the dosage may be about 0.01 mg/kg, about 0.01 mg/kg, about 0.1 mg/kg, about 0.5 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 15 mg/kg, about 20 mg/kg, about 25 mg/kg, about 30 mg/kg, or higher of sterubin.

The dosage may be a single one or a series of two or more doses given in the course of one or more days, as is appropriate for the individual subject. In some embodiments, the composition is administered until symptoms subside or the patient's condition improves, or for a period of continuous therapy, for example for about one day, two days, three days or more, or a week or more (e.g., one week, two weeks, three weeks, or more), or indefinitely for maintenance. In some embodiments, the combination can be administered, sprayed or inhaled one time per day, two times per day, three times per day, or more, or continuously.

As is understood by those of skill in the art, in certain situations it may be necessary to administer the compounds disclosed herein in amounts that exceed the above-stated, preferred dosage range in order to effectively treat a subject.

Unit dosage forms can also be provided, e.g., individual tablets or capsules or individual vials with a premeasured amount of the composition, configured for administration on a predetermined schedule. Unit dosage forms configured for administration one to three times a day are preferred; however, in certain embodiments it is desirable to configure the unit dosage form for administration more than three times a day, or less than one time per day, or for continuous administration.

Dosage amount and interval are adjusted to the individual subject to provide plasma levels of the active moiety which are sufficient to maintain predetermined parameters, indicators, or marker values, or minimal effective concentration (MEC). Dosages necessary to achieve the desired result will depend on individual characteristics and route of administration. However, assays, for example, HPLC assays or bioassays, may be used to determine serum concentrations.

To take advantage of the benefits as described herein, the formulations can be in a form of a supplement, medical food, food additive, food fortifier, beverage additive, beverage fortifier, sublingual composition, or pharmaceutical composition, or in any form as described herein, including as a tablet, encapsulated pill, gelcap pill, chewing gum, liquid suspension, spray, powder, or inhalable or transdermal or transcutaneous or transmucosal substance.

The formulations can support improved, infant-neurogenesis, support brain enzyme and hormone balance, and support termination of CNS, protein folding pathogenic inhibitors. The formulations can also support a positive reduction of toxic plaque, support short term memory, and support neuro-psychological emotional state.

EXAMPLES

Chewable Tablet

In one embodiment, the functional targeting compound is provided in the form of a chewable tablet. The functional targeting compound is sterubin (7-methoxy-3',4',5-trihydroxyflavanone), a flavanone extracted from Yerba Santa (*Eriodictyon californicum*). Sterubin can advantageously be obtained by cryogenic ethanol extraction from the Yerba Santa plant. While any suitable excipients or carriers can be provided, a base transport sub-formula can advantageously be employed comprising: 1) dextrose, natural flavor, rose hips powder, black current powder, green pepper powder, citrus pectin, potassium chloride, magnesium oxide (excipient); 2) hemp seed extract/omega 3, 6 & 9 (17%/18%, 46%, 19%); and glycerin. 91% of component 1) (an excipient) can be combined with 9% of component 2), component 3, and sterubin concentrate. Component 2), component 3), and sterubin are combined in a ratio of 30:34:36 by weight. All percentages refer to parts/100 by % mass.

The chewable tablet is administered to a patient in an amount of 1 tablet per day. Functional magnetic resonance imaging (fMRI), positron emission tomography (PET), in vitro/in vivo research and anecdotal human response validates: 1) a positive reduction of toxic plaque, 2) improved short term memory, and 3) improved neuro-psychological emotional state.

Cellular Chaperone Boosting Supplement

In one embodiment the supplement is Blood Brain Barrier Active (administered at a dosage of 300 mg, preferably once per day, although in certain circumstances it can be administered multiple times per day, e.g., twice, three times, or more), in sublingual form for absorption under the tongue, e.g., as a spray. It contains the following components: 1) Sterubin-bio-concentrated, Yerba Santa (11.2 wt. %); 2) Gamma aminobutyric acid (10.7 wt. %); 3) tauroursodeoxycholic acid (10.7 wt. %); 4) Glutathione (9.7 wt. %); 5) Nicotinamide mononucleotide (9.5 wt. %); 6) Alpha-glyceryl phosphorylcholine (8.5 wt. %); 7) 5-hydroxytryptophan (5.5 wt. %); 8) Phosphatidylserine (4.8 wt. %); 9) Star Anis (2.5 wt. %); 10) Omega oil (11.5 wt. %); 11) Glycerin (11.4 wt. %); 12) Monk Fruit (2.8 wt. %); and 13) Magnesium Stearate (1.2 wt. %). Total Active Ingredients (1-9)=73.1% by weight; Total Excipients (10-13)=26.9% by weight.

In one form, the supplement is an oral spray, e.g., one that may be classified as a FDA "supplement". Delivery devices as known in the art can be employed, e.g., spray bottle, or other suitable delivery device. Suitable delivery devices may possess one or more of the following properties: inexpensive, disposable, mechanically-actuated, nano-misting, capable of delivering a very small volume, and non-refillable. The fluid components of the formulation are preferably 100% FDA recognized, GRAS substances. The mist delivered is a highly effective BBB permeating escort, to provide a bridging platform for the supplement stack which is designed to provide or support: 1) improved, infant-neurogenesis, 2) measurably improved brain enzyme and hormone balance, and/or 3) terminate CNS, protein folding pathogenic inhibitors.

With respect to termination of CNS, protein folding pathogenic inhibitors, evidence supports findings that many neurological diseases are primarily caused by virus and/or bacterial pathogens. The formulations as described herein can inhibit or disrupt these processes, thereby supporting improved health. The formulations promote variable, proteostasis by stimulating chaperone, HSP spectrum to balance proper protein folding while providing a stream of beneficial neurotransmitters to mitigate stressors.

Pre-Clinical Test Data

Cellular Chaperone Boosting Supplement was administered to a patient diagnosed with early Parkinson's Disease (male, age mid 70's). After 10 doses of Cellular Chaperone Boosting Supplement, his right hand tremor completely stopped and he was able to again write with his right hand.

Cellular Chaperone Boosting Supplement was administered to a patient diagnosed with early onset dementia spectrum disorder (male, age early 70's). After daily doses for 30 days, his recall and Alzheimer's intake test results were dramatically improved.

The above description presents the best mode contemplated for carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above that are fully equivalent. Consequently, this invention is not limited to the particular embodiments disclosed. On the contrary, this invention covers all modifications and alternate constructions coming within the spirit and scope of the invention as generally expressed by the following claims, which particularly point out and distinctly claim the subject matter of the invention. While the disclosure has been illustrated and described in detail in the drawings and foregoing description, such illustration and description are to be considered illustrative or exemplary and not restrictive.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article 'a' or 'an' does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It is further understood by those within the art that if a specific number of an introduced claim recitation is intended, such an intent is explicitly recited in the claim, and in the absence of such recitation no such intent is present. For example, as an aid to understanding, the following appended claims may contain usage of the introductory phrases 'at least one' and "one or more" to introduce claim recitations. However, the use of such phrases should not be construed to imply that the introduction of a claim recitation by the indefinite articles 'a' or 'an' limits any particular claim containing such introduced claim recitation to embodiments containing only one such recitation, even when the same claim includes the introductory phrases 'one or more' or 'at least one' and indefinite articles such as 'a' or 'an' (e.g., 'a' and/or 'an' should typically be interpreted to mean 'at least one' or 'one or more'); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of 'two recitations,' without other modifiers, typically means at least two recitations, or two or more recitations). Furthermore, in those instances where a convention analogous to 'at least one of A, B, and C, etc.' is used, in general such a construction is intended in the sense one having skill in the art would understand the convention (e.g., 'a system having at least one of A, B, and C' would include but not be limited to systems that have A alone, B alone, C alone, A and B together, A and C together, B and C together, and/or A, B, and C together, etc.). In those instances where a convention analogous to 'at least one of A, B, or C, etc.' is used, in general such a construction is intended in the sense one having skill in the art would understand the convention (e.g., 'a system having at least one of A, B, or C' would include but not be limited to systems that have A alone, B alone, C alone, A and B together, A and C together, B and C together, and/or A, B, and C together, etc.). It is further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase 'A or B' is understood to include the possibilities of 'A' or 'B' or 'A and B.'

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Any percentages, ratios or other quantities referred to herein are on a weight basis, unless otherwise indicated.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A composition comprising:
    sterubin; and
    a pharmaceutically or physiologically-acceptable carrier;
    wherein the composition is in a form adapted for sublingual administration of a dosage of the composition of 300 mg;
    wherein the composition contains:
        sterubin-bio-concentrated, yerba santa (11.2 wt. %);
        gamma aminobutyric acid (10.7 wt. %);
        tauroursodeoxycholic acid (10.7 wt. %);
        glutathione (9.7 wt. %);
        nicotinamide mononucleotide (9.5 wt. %);
        alpha-glyceryl phosphorylcholine (8.5 wt. %);
        5-hydroxytryptophan (5.5 wt. %);
        phosphatidylserine (4.8 wt. %);
        star anis (2.5 wt. %);
        omega oil (11.5 wt. %);
        glycerin (11.4 wt. %);
        monk fruit (2.8 wt. %); and
        magnesium stearate (1.2 wt. %).

2. The composition of claim 1, in a form of a chewable tablet.

3. The composition of claim 1, in a form of a spray for oral administration.

4. The composition of claim 1, in a form adapted to be delivered to a patient by inhalation in a form of a vapor, a mist, or an aerosol.

5. The composition of claim 1, in a form of a pharmaceutical composition, a dietary supplement, or a health supplement.

6. A method of treatment of a central nervous system disease selected from the group consisting of Parkinson's disease, multiple sclerosis, and dementia, comprising:
    administering, to a patient in need thereof, an effective amount of sterubin;
    wherein the sterubin is administered in a form adapted for sublingual administration of a dosage of a composition of 300 mg;
    wherein the composition contains:
        sterubin-bio-concentrated, yerba santa (11.2 wt. %);
        gamma aminobutyric acid (10.7 wt. %);
        tauroursodeoxycholic acid (10.7 wt. %);
        glutathione (9.7 wt. %);
        nicotinamide mononucleotide (9.5 wt. %);
        alpha-glyceryl phosphorylcholine (8.5 wt. %);
        5-hydroxytryptophan (5.5 wt. %);
        phosphatidylserine (4.8 wt. %);
        star anis (2.5 wt. %);
        omega oil (11.5 wt. %);
        glycerin (11.4 wt. %);
        monk fruit (2.8 wt. %); and
        magnesium stearate (1.2 wt. %).

7. The method of claim 6, wherein the dementia is selected from the group consisting of Alzheimer's disease and lewy body dementia.

8. A method of ameliorating or slowing onset of a condition characterized by formation of amyloid plaque and/or tau plaque, comprising:
    administering, to a patient in need thereof, an effective amount of sterubin;
    wherein the sterubin is administered in a form adapted for sublingual administration of a dosage of a composition of 300 mg;
    wherein the composition contains:
        sterubin-bio-concentrated, yerba santa (11.2 wt. %);
        gamma aminobutyric acid (10.7 wt. %);
        tauroursodeoxycholic acid (10.7 wt. %);
        glutathione (9.7 wt. %);
        nicotinamide mononucleotide (9.5 wt. %);
        alpha-glyceryl phosphorylcholine (8.5 wt. %);
        5-hydroxytryptophan (5.5 wt. %);
        phosphatidylserine (4.8 wt. %);
        star anis (2.5 wt. %);
        omega oil (11.5 wt. %);
        glycerin (11.4 wt. %);
        monk fruit (2.8 wt. %); and
        magnesium stearate (1.2 wt. %).

9. A method of supporting brain health or brain function, comprising:
    administering, to a patient in need thereof, an effective amount of sterubin;
    wherein the sterubin is administered in a form adapted for sublingual administration of a dosage of a composition of 300 mg;
    wherein the composition contains:
        sterubin-bio-concentrated, yerba santa (11.2 wt. %);
        gamma aminobutyric acid (10.7 wt. %);
        tauroursodeoxycholic acid (10.7 wt. %);
        glutathione (9.7 wt. %);
        nicotinamide mononucleotide (9.5 wt. %);
        alpha-glyceryl phosphorylcholine (8.5 wt. %);
        5-hydroxytryptophan (5.5 wt. %);
        phosphatidylserine (4.8 wt. %);
        star anis (2.5 wt. %);
        omega oil (11.5 wt. %);
        glycerin (11.4 wt. %);
        monk fruit (2.8 wt. %); and
        magnesium stearate (1.2 wt. %).

10. The method of claim 6, wherein the composition is in a form of a chewable tablet or a spray for oral administration.

11. The method of claim 6, wherein the composition is in a form of a pharmaceutical composition, a dietary supplement, or a health supplement.

12. The method of claim 8, wherein the composition is in a form of a chewable tablet or a spray for oral administration.

13. The method of claim 8, wherein the composition is in a form of a pharmaceutical composition, a dietary supplement, or a health supplement.

14. The method of claim 9, wherein the composition is in a form of a chewable tablet or a spray for oral administration.

15. The method of claim 9, wherein the composition is in a form of a pharmaceutical composition, a dietary supplement, or a health supplement.

* * * * *